(12) United States Patent
Sliwa

(10) Patent No.: US 11,931,749 B2
(45) Date of Patent: Mar. 19, 2024

(54) DISPENSER FOR DISPENSING LIQUIDS

(71) Applicant: Gerresheimer Boleslawiec Spolka Akcyjna, Boleslawiec (PL)

(72) Inventor: Mateusz Sliwa, Lwowek Slaski (PL)

(73) Assignee: Gerresheimer Boleslawiec Spolka Akcyjna, Boleslawiec (PL)

(*) Notice: Subject to any disclaimer, the term of this patent is extended or adjusted under 35 U.S.C. 154(b) by 0 days.

(21) Appl. No.: 17/880,282

(22) Filed: Aug. 3, 2022

(65) Prior Publication Data

US 2024/0042464 A1    Feb. 8, 2024

(51) Int. Cl.
| | |
|---|---|
| *B05B 1/02* | (2006.01) |
| *A61F 9/00* | (2006.01) |
| *B05B 13/02* | (2006.01) |

(52) U.S. Cl.
CPC .............. *B05B 1/02* (2013.01); *A61F 9/0008* (2013.01); *B05B 13/0278* (2013.01)

(58) Field of Classification Search
CPC ..... B05B 1/02; B05B 13/0278; A61F 9/0008; B01L 3/0241; B65D 47/18; B65D 1/08
USPC ................................................. 222/420, 212
See application file for complete search history.

(56) References Cited

U.S. PATENT DOCUMENTS

| | | | | |
|---|---|---|---|---|
| 2,987,223 A | * | 6/1961 | Armour .................. | B65D 47/18 222/207 |
| 5,056,689 A | * | 10/1991 | Heyl ...................... | A61F 9/0008 222/190 |
| 5,219,101 A | * | 6/1993 | Matkovich ............. | B65D 47/18 210/321.64 |
| 5,431,314 A | * | 7/1995 | Bonnelye ............... | B65D 47/18 604/298 |
| 5,496,471 A | * | 3/1996 | Heyl ...................... | A61F 9/0008 222/190 |
| 5,588,559 A | * | 12/1996 | Vallet Mas ............. | A61J 1/145 222/190 |

(Continued)

FOREIGN PATENT DOCUMENTS

| | | |
|---|---|---|
| EP | 3059181 | 8/2016 |
| EP | 3858303 | 8/2021 |

(Continued)

OTHER PUBLICATIONS

Extended European Search Report in European Appln. No. 20020644. 9, dated Jun. 11, 2021, 8 pages.

*Primary Examiner* — Paul R Durand
*Assistant Examiner* — Michael J. Melaragno
(74) *Attorney, Agent, or Firm* — Fish & Richardson P.C.

(57) ABSTRACT

A dispenser for dispensing liquids, in particular ophthalmic liquids, for dispensing the medicine as individual drops is mounted on the neck of a reservoir, e.g., a bottle, and it is made of a flange connected to a bushing and with a domed tip situated on the opposite side of the bushing, the flange being fitted onto the neck of the reservoir and the bushing entering the neck of the reservoir, while a dispensing domed tip comprising a dispensing opening protrudes outside the reservoir. Inside the bushing and the domed tip there is a conical element placed therein, blocking the flow of liquids, the opening in the domed tip having an inner flange. The conical element has a flange at the base of the cone. The flange situated in the dispensing domed tip is ended from the inside with a fin directed towards the conical element blocking the flow of liquids.

17 Claims, 2 Drawing Sheets

(56) References Cited

U.S. PATENT DOCUMENTS

| | | | |
|---|---|---|---|
| 5,845,814 A | 12/1998 | Nobbio | |
| 5,992,701 A * | 11/1999 | Bougamont | B65D 47/18 222/189.09 |
| 6,612,469 B2 * | 9/2003 | Lopez Pardo | B65D 47/18 222/420 |
| 6,662,977 B2 * | 12/2003 | Gerber | B65D 47/122 222/494 |
| 6,766,816 B2 * | 7/2004 | Secondo | B05B 11/0072 137/853 |
| 7,306,129 B2 * | 12/2007 | Swiss | B65D 47/205 222/326 |
| 7,513,396 B2 * | 4/2009 | Pardes | B65D 47/205 222/326 |
| 7,997,460 B2 * | 8/2011 | Pardes | A61M 11/008 222/326 |
| 8,517,222 B2 * | 8/2013 | Painchaud | A61J 1/1425 222/212 |
| 2005/0173456 A1 | 8/2005 | Backes | |
| 2005/0184104 A1 * | 8/2005 | Mutterle | B65D 47/18 222/546 |
| 2005/0279779 A1 * | 12/2005 | Gerondale | B65D 47/18 222/420 |
| 2006/0111680 A1 * | 5/2006 | Spada | B65D 47/18 604/295 |
| 2007/0028988 A1 * | 2/2007 | Mihashi | B65D 23/02 139/383 A |
| 2007/0164051 A1 * | 7/2007 | Mijers | B65D 47/18 222/189.09 |
| 2007/0233021 A1 * | 10/2007 | Poisson | A61M 35/003 604/295 |
| 2011/0297703 A1 * | 12/2011 | Wilson | B65D 47/18 222/571 |
| 2019/0307641 A1 * | 10/2019 | Golub | B65D 41/20 |
| 2020/0324945 A1 * | 10/2020 | Song | A61M 35/003 |
| 2021/0169688 A1 * | 6/2021 | Bader | A61M 3/0262 |

FOREIGN PATENT DOCUMENTS

| | | | | |
|---|---|---|---|---|
| FR | 2934569 | 2/2010 | | |
| FR | 2941682 | 8/2010 | | |
| PL | 426592 | 2/2020 | | |
| PL | 432828 | 2/2020 | | |
| WO | WO-2008099079 A2 * | 8/2008 | | A61F 99/0008 |
| WO | WO-2013075256 A1 * | 5/2013 | | A61F 9/0008 |
| WO | WO-2015181730 A1 * | 12/2015 | | A61F 9/0008 |
| WO | WO-2018206386 A1 * | 11/2018 | | A61F 9/0008 |
| WO | WO-2020198655 A1 * | 10/2020 | | A61F 9/0008 |
| WO | WO-2022033705 A1 * | 2/2022 | | |

* cited by examiner

DISPENSER FOR DISPENSING LIQUIDS

TECHNICAL FIELD

The object of the invention is a dispenser for dispensing liquids, in particular ophthalmic liquids, where the medicine is usually dispensed as individual drops.

BACKGROUND

There is a known dispenser for dispensing liquids, in particular ophthalmic liquids, presented in the description of application of the invention in published Polish Application PL426592. This dispenser is mounted on the neck of a reservoir, in particular a bottle, and it is made of a flange fitted onto the neck of the reservoir and connected to the flange of a bushing entering the neck of the reservoir, and also connected to the flange of a portion closing the neck of the reservoir, which in its central zone has a cylindrical tongue entering the neck of the reservoir, while a narrow opening is formed in the axis of the tongue. Dispensers according to this application are characterised in that a cylindrical recess is formed in the axis of the tongue, in which an inset is placed, made of foamed plastic, preferably polyethylene or polypropylene. The inset of foamed plastic has pores 7-30 micrometres in size. The recess for the inset has the following dimensions: diameter 1.5-2.5 mm, length 2.5-4.5 mm.

DETAILED DESCRIPTION

The dispenser for dispensing liquids, in particular ophthalmic liquids, according to the invention, is mounted on the neck of a reservoir, in particular a bottle; it is made of a flange connected to a bushing and with a domed tip situated on the opposite side of the bushing, the flange being fitted onto the neck of the reservoir and the bushing entering the neck of the reservoir, while a dispensing domed tip comprising a dispensing opening protrudes outside the reservoir. The dispenser is characterised in that inside the bushing and the domed tip there is a conical element placed therein, blocking the flow of liquids, the opening in the domed tip having an inner flange. The conical blocking element has a flange at the base of the cone. The flange situated in the dispensing domed tip is ended from the inside with a fin directed towards the conical element blocking the flow of liquids. The fin directed towards the conical element blocking the flow of liquids has a local gap with the following dimensions: A from 0.3 to 0.6 mm and B from 0.3 to 0.6 mm. In the place of connection to the domed tip, the bushing has a flange constituting a stop for the conical element, wherein in the flange there is a cut-out with the following dimensions: C from 0.3 to 0.6 mm, D from 0.3 to 0.6 mm and E from 0.3 to 0.6 mm The dispenser for dispensing liquids according to the invention is characterised by its extremely simple structure, and at the same time good functionality, since it allows the dispensing of individual drops of liquids without any problems. This has been achieved due to the use of two flanges disposed separately and the inside placement of a conical element blocking the flow of liquids, which constitutes an obstruction for the free outflow of liquids, and at the same time it allows the outflow of a very small amount of a liquid in the form of a drop. At the same time, this element does not require such precise construction as elements in other dispensers. Moreover, it allows the free flow of air after the action of dispensing a liquid. The design of the dispenser allows avoiding high costs resulting from complicated dispensing structures and complicated structures introducing air into the reservoir.

Figure 1:
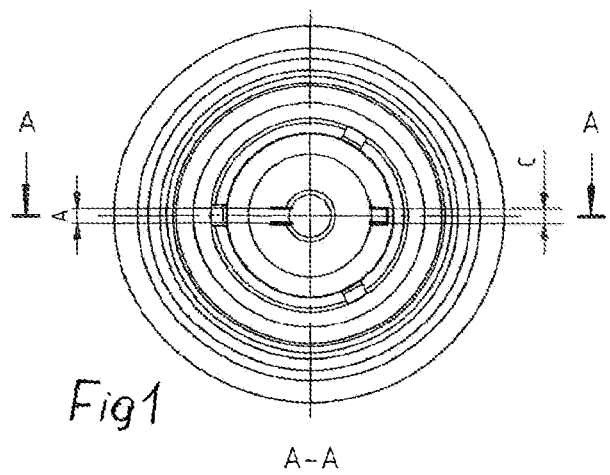
FIG. 1 presents the dispenser in a top view.
Figure 2:
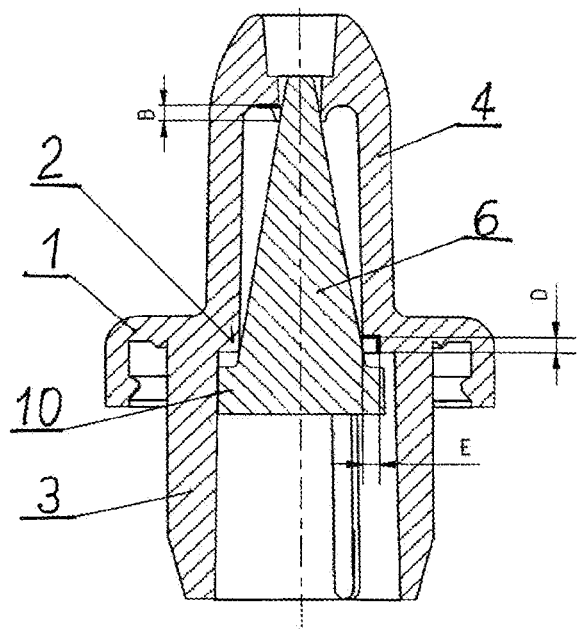
FIG. 2 presents the dispenser in a lengthwise section along the line A-A.
Figure 3:
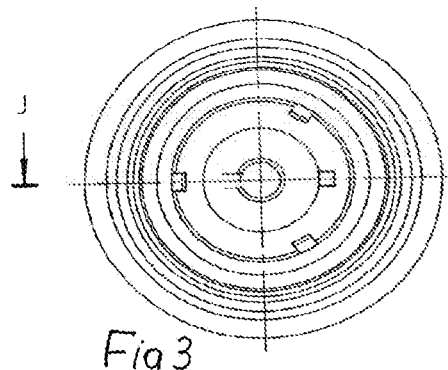
FIG. 3 is a view of the dispenser without the conical element blocking the flow of liquids, FIG. 4 constitutes a cross-section of the dispenser of FIG. 3 along the line J-J.
Figure 4:
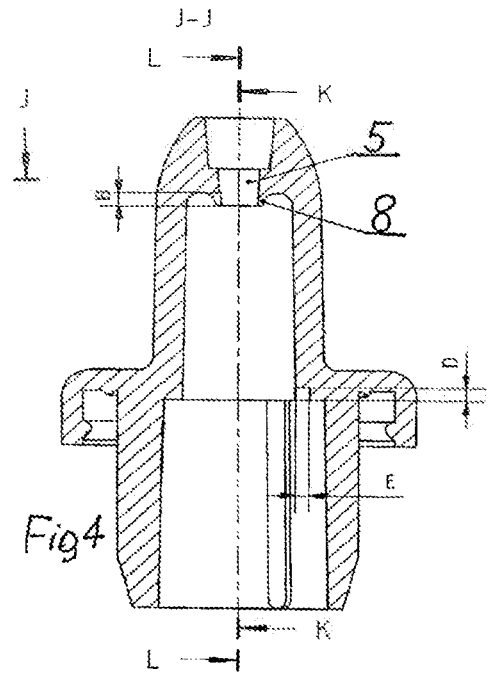
Figure 5:
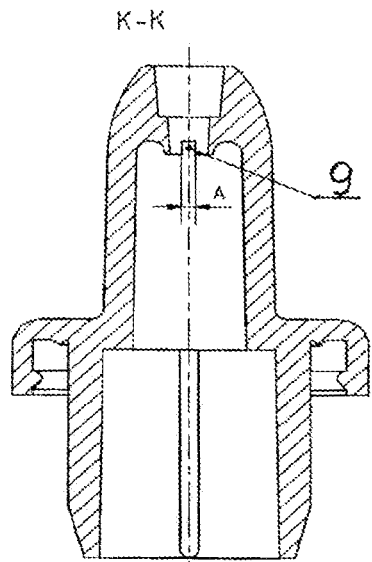
FIG. 5 is a cross-section of the dispenser of FIG. 3 along the line K-K.
Figure 6:
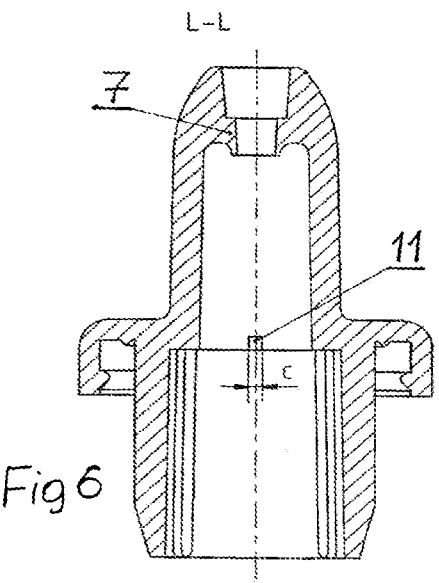
FIG. 6 is a cross-section of the dispenser of FIG. 3 along the line L-L.

The dispenser for dispensing liquids according to the invention is described more closely in an embodiment and in the drawing, in which FIG. 1 presents the dispenser in a top view, FIG. 2 presents the dispenser in a lengthwise section along the line A-A, FIG. 3 is a view of the dispenser without the conical element blocking the flow of liquids, FIG. 4 constitutes a cross-section of the dispenser of FIG. 3 along the line J-J, FIG. 5 is a cross-section of the dispenser of FIG. 3 along the line K-K, while FIG. 6 is a cross-section of the dispenser of FIG. 3 along the line L-L.

As presented in FIG. 1 to FIG. 6, the dispenser for dispensing ophthalmic liquids according to the invention is made of a flange 1 connected to a bushing 3 and to a domed tip 4 situated on the opposite side of the bushing 3. The flange 1 is fitted onto the neck of a reservoir. The flange 1 is connected to the flange 2 of the bushing 3, which is placed in the neck of the reservoir. The domed tip 4 comprises a dispensing opening 5 inside it. The conical element 6 blocking the flow of liquids is placed inside the bushing 3 and the dispensing domed tip 4. The opening 5 in the dispensing domed tip 4 has an inner flange 7. The flange 7 situated in the dispensing domed tip 4 is ended from the inside with a fin 8 directed towards the conical element 6 blocking the flow of liquids. The fin 8 has a local gap 9, whose dimension A amounts to 0.4 mm, while its dimension B amounts to 0.3 mm. At the base of the cone, the conical element 6 has a flange 10, which during dispensing leans against the flange 2 of the bushing 3. In the flange 2 there is a cut-out with the following dimensions: C=0.4 mm, D=0.4 mm and E=0.3 mm. The dispensed medicine seeps through this cut-out.

The use of the dispenser proceeds as follows. The dispenser is fitted onto a reservoir, which is not shown in the drawing, and in particular onto its neck. The reservoir is filled with a proper liquid intended to cure the eye to which the medicine is to be delivered in the form of a single drop. To this end, the reservoir with the fitted dispenser is turned upside down. The liquid contained in the reservoir pushes against the flange 10 of the conical element 6, due to which it closes the outflow of the liquid from the reservoir and thus from the dispenser. The liquid can only seep through the cut-out between the flange 10 and the flange 2 and through the local gap 9. This means that the outflow of the curing liquid from the reservoir is obstructed in two places, due to which it is much easier to achieve a single drop, and also the construction of individual elements of the dispenser does not require the precision of previous solutions.

What is claimed is:

1. A dispenser for dispensing ophthalmic liquids that is configured for being mounted on a neck of an ophthalmic liquids reservoir, comprising:

an exterior flange protruding from a bushing, the exterior flange being configured to be fitted onto the neck of the reservoir to mount the dispenser to the reservoir with the bushing entering the neck of the reservoir, the bushing having an interior flange with a cut-out in a radially inner surface of the interior flange;

a dispensing domed tip situated on the opposite side of the bushing so that, when the exterior flange is connected to the neck of the reservoir, the domed tip protrudes outside the reservoir, the domed tip comprising a dispensing opening through to an interior of the domed tip and an inner flange which extends radially inward from the domed tip, the inner flange comprising a fin along an inner longitudinal end of the inner flange, the fin extending axially from the inner flange toward the bushing, the fin having a local gap along the inner longitudinal end of the inner flange; and a conical element inside the bushing and the domed tip, the conical element configured to insert into the dispensing opening in the inner flange of the domed tip to block flow of liquids through the dispensing opening by abutting an interior surface of the fin, the conical element also configured to abut the interior flange of the bushing and block flow of liquids through the domed tip, the cut-out in the bushing and the local gap in the fin configured to allow a limited amount of liquid to seep through to dispense an individual drop of liquid at the dispensing opening.

2. The dispenser according to claim 1, wherein the conical element comprises an outer flange at a base of the conical element, the outer flange configured to abut the interior flange of the bushing when blocking flow.

3. The dispenser according to claim 1, wherein the local gap has the following dimensions: a width in a circumferential direction of from 0.3 to 0.6 mm and a height in an axial direction from 0.3 to 0.6 mm.

4. The dispenser according to claim 3, wherein the cut-out has the following dimensions: a width in a circumferential direction of from 0.3 to 0.6 mm, a height in an axial direction of from 0.3 to 0.6 mm and a depth in a radial direction of from 0.3 to 0.6 mm.

5. The dispenser according to claim 2, wherein the conical element is configured, when the dispenser is fitted to a reservoir and the reservoir positioned with the dispenser oriented downward, so that liquid in the reservoir pushes against the outer flange of the conical element, closing outflow of the liquid from the dispenser.

6. The dispenser according to claim 1, wherein the cut-out has the following dimensions: a width (C) in a circumferential direction from 0.3 to 0.6 mm, a height D) in an axial direction from 0.3 to 0.6 mm, and a depth (E) in a radial direction from 0.3 to 0.6 mm.

7. The dispenser according to claim 1, wherein the interior of the inner flange, including the fin, is frustoconical having its narrowest diameter oriented toward the conical element.

8. The dispenser according to claim 7, wherein the conical element is conical in a portion that abuts the fin when the conical element blocks the flow of liquids through the domed tip.

9. The dispenser according to claim 8, wherein the conical element abuts the interior surface of the fin and the interior flange of the bushing concurrently.

10. The dispenser according to claim 1, wherein the conical element is recessed within the domed tip when abutting the fin.

11. The dispenser according to claim 10, wherein the dispensing opening is frustoconical.

12. The dispenser according to claim 1, wherein where the conical element is conical in a portion that abuts the fin when the conical element blocks the flow of liquids through the domed tip.

13. The dispenser according to claim 1, wherein the conical element abuts the interior surface of the fin and the interior flange of the bushing concurrently.

14. The dispenser according to claim 1, wherein the conical element has its largest diameter adjacent the interior flange of the bushing and its smallest diameter adjacent the fin.

15. The dispenser according to claim 1, where the conical element comprises an outer flange at a base of the conical element, the outer flange having an outer diameter larger than a diameter of the radially inner surface of the interior flange of the bushing.

16. The dispenser according to claim 1, wherein the fin is integrally formed with the inner flange of the domed tip, the fin at least partially defining the dispensing opening of the domed tip.

17. The dispenser according to claim 1, wherein the fin comprises a height in an axial direction from 0.3 to 0.6 mm.

* * * * *